(12) United States Patent
Dickie (10) Patent No.: US 11,497,479 B2
(45) Date of Patent: Nov. 15, 2022

(54) METHOD AND SYSTEM FOR CONTROLLING SETTINGS OF AN ULTRASOUND SCANNER

(71) Applicant: Clarius Mobile Health Corp., Burnaby (CA)

(72) Inventor: Kris Dickie, Vancouver (CA)

(73) Assignee: Clarius Mobile Health Corp., Vancouver (CA)

( * ) Notice: Subject to any disclaimer, the term of this patent is extended or adjusted under 35 U.S.C. 154(b) by 55 days.

(21) Appl. No.: 16/870,936

(22) Filed: May 9, 2020

(65) Prior Publication Data

US 2021/0345993 A1 Nov. 11, 2021

(51) Int. Cl.
| | |
|---|---|
| *A61B 8/00* | (2006.01) |
| *G01S 7/52* | (2006.01) |
| *A61B 8/08* | (2006.01) |
| *A61B 8/10* | (2006.01) |

(52) U.S. Cl.
CPC ............... *A61B 8/585* (2013.01); *A61B 8/08* (2013.01); *A61B 8/0808* (2013.01); *A61B 8/0825* (2013.01); *A61B 8/0866* (2013.01); *A61B 8/0875* (2013.01); *A61B 8/0883* (2013.01); *A61B 8/0891* (2013.01); *A61B 8/10* (2013.01); *A61B 8/54* (2013.01); *G01S 7/5205* (2013.01); *G01S 7/52096* (2013.01)

(58) Field of Classification Search
CPC ......... A61B 8/585; A61B 8/08; A61B 8/0808; A61B 8/0825; A61B 8/0866; A61B 8/0875; A61B 8/0883; A61B 8/0891; A61B 8/10; A61B 8/54; G01S 7/5205; G01S 7/52096
See application file for complete search history.

(56) References Cited

U.S. PATENT DOCUMENTS

| | | | |
|---|---|---|---|
| 9,408,591 B2 | 8/2016 | Kotaki et al. | |
| 9,691,167 B1 | 6/2017 | Frenkel et al. | |
| 10,588,596 B2 | 3/2020 | Dickie et al. | |
| 2009/0149752 A1 | 6/2009 | Osaka et al. | |
| 2010/0274103 A1* | 10/2010 | Snook | A61B 8/00 600/301 |
| 2018/0144214 A1 | 5/2018 | Hsieh et al. | |

(Continued)

OTHER PUBLICATIONS

Examination Notes, International Search Report and Written Opinion of the International Searching Authority for corresponding PCT International Application No. PCT/CA2021/050643 filed May 7, 2021.

*Primary Examiner* — Joseph M Santos Rodriguez
*Assistant Examiner* — Kaitlyn E Sebastian
(74) *Attorney, Agent, or Firm* — Julian Ho (57) ABSTRACT

During acquisition of an ultrasound image feed, ultrasound control data frames are acquired that may be interspersed amongst the ultrasound data frames. The control data frames may use consistent reference scan parameters, irrespective of the scanner settings, and may not need to be converted to image frames. The control data frames can be passed to an artificial intelligence model, which predicts the suitable settings for scanning the anatomy that is being scanned. The artificial intelligence model can be trained with a dataset containing different classes of ultrasound control data frames for different settings, where substantially all the ultrasound control data frames in the dataset are consistently acquired using the reference scan parameters.

19 Claims, 3 Drawing Sheets

(56) References Cited

U.S. PATENT DOCUMENTS

2018/0220995 A1* 8/2018 Pelissier ............... A61B 8/54
2018/0263593 A1* 9/2018 Dickie ............... A61B 8/0841
2019/0175149 A1* 6/2019 Dickie ............... A61B 8/4444
2019/0326007 A1 10/2019 Sharma et al.
2019/0350564 A1* 11/2019 Gajdos ............... A61B 8/565

* cited by examiner

METHOD AND SYSTEM FOR CONTROLLING SETTINGS OF AN ULTRASOUND SCANNER

TECHNICAL FIELD

This disclosure relates to viewing ultrasound images. In particular, it relates to systems and methods for controlling settings of an ultrasound scanner.

BACKGROUND

Ultrasound is a useful, non-invasive imaging technique capable of producing real time images of internal structures within tissue. Ultrasound imaging has an advantage over X-ray imaging in that ultrasound imaging does not involve ionizing radiation. Some mobile ultrasound scanners, including app-based ultrasound scanners, require an add-on device that can act as both as a display and a control device. Examples of these add-on devices are mobile phones, tablets, laptops or desktop computers.

When using some ultrasound scanners, whether mobile or not, users are traditionally expected to select a preset depending on the part of the anatomy that is to be scanned. The preset is associated with a set of parameters that instruct the ultrasound scanner how to acquire and process the ultrasound data. The set of parameters for each preset is usually optimized for the particular body part to which the preset relates. There may be upwards of a hundred different parameters (including, for example, frequency, focal zones, line density, whether harmonic imaging is on, and the like) for each preset depending on the ultrasound scanner.

In some cases, for example in an emergency room, in a field hospital, or if a user is unfamiliar with the particular ultrasound scanner, the preset may be incorrectly selected. This may happen for various reasons. For example, this may unintentionally done by the operator, or it may be left on a prior setting, or it may be not set and the scanner left in a default mode. Additionally or alternatively, if different areas of the body need to be scanned in one session, the user may forget to switch the preset when moving to a different body area. The result may be, for example, that the ultrasound image that is generated is not optimal, and/or the ultrasound scanner uses more power than necessary.

There is therefore a need to ensure that a preset of an ultrasound scanner is correctly selected for the part of the anatomy that is being scanned.

The above background information is provided to reveal information believed by the applicant to be of possible relevance to the present invention. No admission is necessarily intended, nor should be construed, that any of the preceding information constitutes prior art against the present invention. The embodiments discussed herein may address and/or ameliorate one or more of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF DRAWINGS

The following drawings illustrate embodiments of the invention and should not be construed as restricting the scope of the invention in any way.

DETAILED DESCRIPTION

A. Glossary

The term "AI model" means a mathematical or statistical model that may be generated through artificial intelligence techniques such as machine learning. For example, the machine learning may involve inputting labeled or classified data into a neural network algorithm for training, so as to generate a model that can make predictions or decisions on new data without being explicitly programmed to do so. Different software tools (e.g., TensorFlow™, PyTorch™, Keras™) may be used to perform machine learning processes.

The term "depth" when relating to an ultrasound image refers to a measure of how far into the structure being scanned (e.g., tissue or a phantom) a given ultrasound image shows.

The term "module" can refer to any component in this invention and to any or all of the features of the invention without limitation. A module may be a software, firmware or hardware module, and may be located, for example, in the ultrasound scanner, a display device or a server.

The term "network" can include both a mobile network and data network without limiting the term's meaning, and includes the use of wireless (e.g. 2G, 3G, 4G, 5G, WiFi™, WiMAX™, Wireless USB (Universal Serial Bus), Zigbee™, Bluetooth™ and satellite), and/or hard wired connections such as local, internet, ADSL (Asymmetrical Digital Subscriber Line), DSL (Digital Subscriber Line), cable modem, T1, T3, fiber-optic, dial-up modem, television cable, and may include connections to flash memory data cards and/or USB memory sticks where appropriate. A network could also mean dedicated connections between computing devices and electronic components, such as buses for intra-chip communications.

The term "operator" (or "user") may refer to the person that is operating an ultrasound scanner (e.g., a clinician, medical personnel, a sonographer, ultrasound student, ultrasonographer and/or ultrasound technician).

The term "processor" can refer to any electronic circuit or group of circuits that perform calculations, and may include, for example, single or multicore processors, multiple processors, an ASIC (Application Specific Integrated Circuit), and dedicated circuits implemented, for example, on a reconfigurable device such as an FPGA (Field Programmable Gate Array). A processor may perform the steps in the flowcharts and sequence diagrams, whether they are explicitly described as being executed by the processor or whether the execution thereby is implicit due to the steps being described as performed by the system, a device, code or a module. The processor, if comprised of multiple processors, may be located together or geographically separate from each other. The term includes virtual processors and machine instances as in cloud computing or local virtualization, which are ultimately grounded in physical processors.

The term "scan convert", "scan conversion", or any of its grammatical forms refers to the construction of an ultrasound media, such as a still image or a video, from lines of ultrasound scan data representing echoes of ultrasound signals. Scan conversion may involve converting beams and/or vectors of acoustic scan data which are in polar (R-theta) coordinates to cartesian (X-Y) coordinates.

The term "system" when used herein, and not otherwise qualified, refers to a system for controlling the settings of an ultrasound scanner using data obtained in control data frames acquired between image data frames, the system being a subject of the present invention. The system may include a scanner and a display device, or a scanner, display device and a server.

The term "ultrasound control data frame" (or "control data frame" for brevity) refers to a frame of ultrasound data that is captured by an ultrasound scanner. The ultrasound control data frame has the form of multiple lines of data that each represent echoes of ultrasound. Ultrasound control data frames may all be acquired with consistent, reference scan parameters, unlike ultrasound data frames, which may be acquired with different parameters depending on the settings of the ultrasound scanner. Ultrasound control data frames are not usually converted to viewable image frames.

The term "ultrasound data frame" (or "image data frame") refers to a frame of ultrasound data that is captured by an ultrasound scanner. The ultrasound data frame typically has the form of multiple lines of data that each represent echoes of ultrasound. Ultrasound data frames are usually acquired with different sets of scan parameters, where each set depends on which preset of the ultrasound scanner is selected. Ultrasound data frames are usually converted to viewable image frames for viewing by an operator of the ultrasound scanner.

The term "ultrasound image frame" (or "image frame") refers to a frame of post-scan conversion data that is suitable for rendering an ultrasound image on a screen or other display device.

B. Exemplary Embodiments

Figure 1:
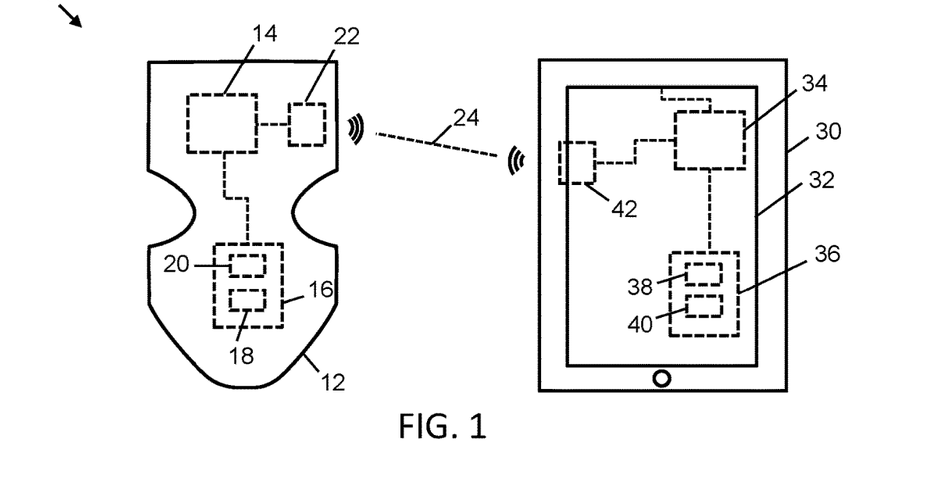
FIG. 1 is a schematic diagram of a system according to an embodiment of the present invention.

Referring to FIG. 1, an exemplary system 10 is shown for controlling the settings of an ultrasound scanner 12 (hereinafter "scanner" for brevity) dependent on interspersed control data frames. The system 10 includes an ultrasound scanner 12 with a processor 14, which is connected to a non-transitory computer readable memory 16 storing computer readable instructions 18, which, when executed by the processor 14, may cause the scanner 12 to provide one or more of the functions of the system 10. Such functions may be, for example, the acquisition of ultrasound data, the processing of ultrasound data, the conversion of ultrasound data, the transmission of ultrasound data or images to a display device 30, the detection of operator inputs to the scanner 12, and/or the switching of the settings of the scanner 12.

Also stored in the computer readable memory 16 may be computer readable data 20, which may be used by the processor 14 in conjunction with the computer readable instructions 18 to provide the functions of the system 10. Computer readable data 20 may include, for example, configuration settings for the scanner 12, such as presets that instruct the processor 14 how to collect and process the ultrasound data for a given body part. Such a preset may be selected, for example, depending on the processing of a control data frame against an AI model that is stored in the computer readable data 20. A preset may include numerous different parameters for the scanner 12.

The scanner 12 includes a communications module 22 connected to the processor 14. In the illustrated example, the communications module 22 wirelessly transmits signals to and receives signals from the display device 30 along wireless communication link 24. The protocol used for communications between the scanner 12 and the display device 30 may be WiFi™ or Bluetooth™, for example, or any other suitable two-way radio communications protocol. The scanner 12 may operate as a WiFi™ hotspot, for example. Communication link 24 may use any suitable wireless network connection. In some embodiments, the communication link between the scanner 12 and the display device 30 may be wired. For example, the scanner 12 may be attached to a cord that may be pluggable into a physical port of the display device 30.

The display device 30 may be, for example, a laptop computer, a tablet computer, a desktop computer, a smart phone, a smart watch, spectacles with a built-in display, a television, a bespoke display or any other display device that is capable of being communicably connected to the scanner 12. The display device 30 may host a screen 32 and may include a processor 34, which is connected to a non-transitory computer readable memory 36 storing computer readable instructions 38, which, when executed by the processor 34, cause the display device 30 to provide one or more of the functions of the system 10. Such functions may be, for example, the receiving of ultrasound data that may or may not be pre-processed; scan conversion of ultrasound data that is received into a ultrasound images; processing of ultrasound data in control data frames and/or image data frames; the display of an ultrasound image on the screen 32; the display of a user interface; the control of the scanner 12; and/or the storage, application, reinforcing and/or training of an AI model.

Also stored in the computer readable memory 36 may be computer readable data 40, which may be used by the processor 34 in conjunction with the computer readable instructions 38 to provide the functions of the system 10. Computer readable data 40 may include, for example, settings for the scanner 12, such as presets for acquiring ultrasound data depending on the analysis of control data frames; settings for a user interface displayed on the screen 32; and/or one or more AI models. Settings may also include any other data that is specific to the way that the scanner 12 operates or that the display device 30 operates.

It can therefore be understood that the computer readable instructions and data used for controlling the system 10 may be located either in the computer readable memory 16 of the scanner 12, the computer readable memory 36 of the display device 30, and/or both the computer readable memories 16, 36.

The display device 30 may also include a communications module 42 connected to the processor 34 for facilitating communication with the scanner 12. In the illustrated example, the communications module 42 wirelessly transmits signals to and receives signals from the scanner 12 on wireless communication link 24. However, as noted, in some embodiments, the connection between scanner 12 and display device 30 may be wired.

Figure 2:
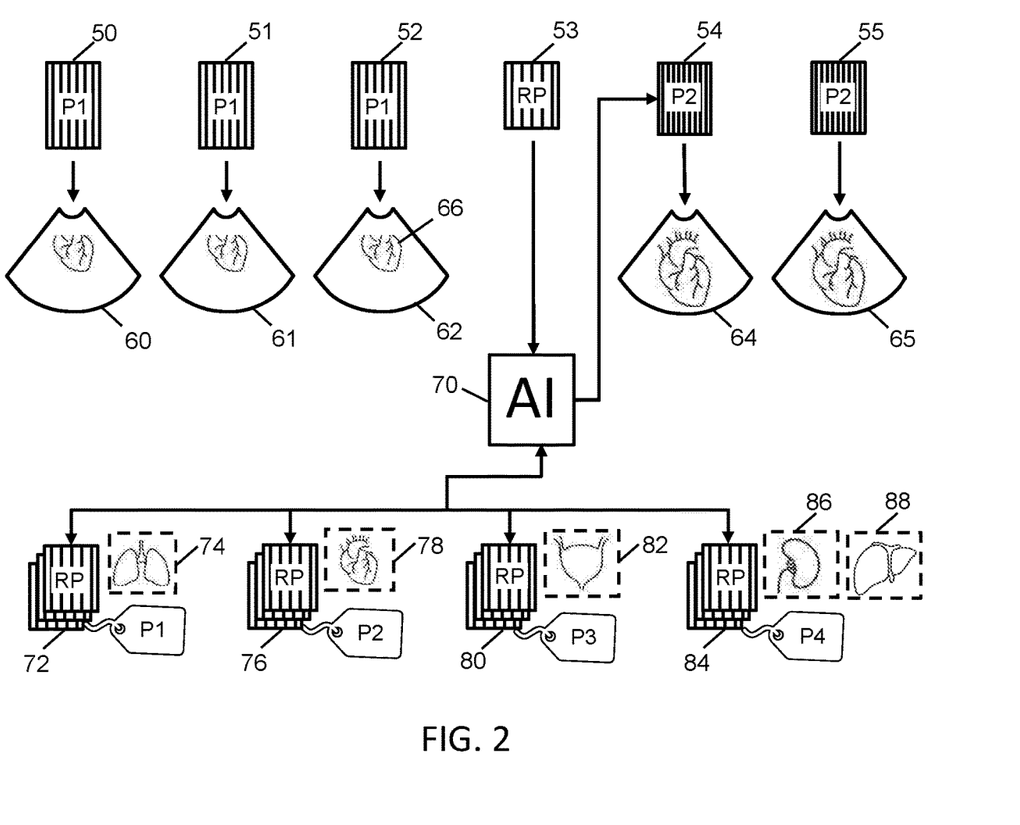
FIG. 2 is a schematic diagram showing a series of control and image frames and their analysis, according to an embodiment of the present invention.

Referring to FIG. 2, shown there generally is a schematic diagram showing a series of control and image frames and their analysis, according to an embodiment of the present invention. In an embodiment, an ultrasound image feed is acquired by obtaining ultrasound data frames that are converted to viewable image frames. During acquisition of the ultrasound image feed, additional ultrasound control data frames may be acquired that are interspersed amongst the ultrasound data frames. The ultrasound control data frames may use reference scan parameters that are consistent, regardless of whatever preset or settings the ultrasound scanner is set to. The ultrasound control data frames may not be converted to image frames for display, and instead are used to control the settings of the ultrasound scanner. This is illustrated in FIG. 2.

Furthermore, the acquisition of the ultrasound control data frames may not necessarily interrupt the regular refresh rate of the displayed ultrasound image feed.

In some cases, ultrasound data frames that are acquired are converted to optimized viewable image frames, which are processed against an additional AI model that identifies anatomical features in the optimized viewable image frames. These features are then highlighted on the displayed, optimized image frames.

In FIG. 2, consecutive image data frames 50, 51, 52 are shown, followed by a control data frame 53, which in turn is followed by two further image data frames 54, 55. The image data frames 50-55 are illustrated as a series of vertical scan lines that represent the image data that may be acquired by the scanner 12. In the example, the image data frames 50-55 are also shown as pre scan-converted scan lines that, for example, have not yet been converted to the reflect a curvature of the transducer array of the ultrasound scanner 12. Image data frame 50 is acquired using a first set of parameters, for example parameters that are set by preset P1. Image data frame 50 may then be scan converted into ultrasound image frame 60 for viewing. Likewise, image data frame 51 may be acquired using the parameters for preset P1 and can also be scan converted into ultrasound image frame 61 for viewing. Image data frame 52 is also acquired using the parameters for preset P1 and converted into ultrasound image frame 62 for viewing. Preset P1 is, in this example, not optimal for the acquisition of ultrasound data for the body part 66 displayed in ultrasound image frames 60, 61, 62.

After the acquisition of a number of image data frames 50, 51, 52, a control data frame 53 may be acquired. The control data frame 53 may use reference parameters RP for acquiring the ultrasound data in the control data frame 53. In general, the reference parameters RP may be configured to be consistent, regardless of whatever preset or settings the ultrasound scanner is set to. This may mean that the reference parameters are different from the parameters of the preset P1 and the other presets that the scanner 12 may be capable of using. For example, as illustrated, the reference parameters used to acquire the control data frame 53 have a shallower depth of scan than the parameters for preset P1 used in the data frames 50, 51, 52. Also, there are fewer data lines (e.g., less line density, as shown via the sparser vertical scan lines) in the control data frame 53 than the parameters for preset P1 used in the image data frames 50, 51, 52.

The control data frame 53 may not be converted to an image frame, but instead is input to an AI model 70 for processing. The AI model 70 may be provided on the scanner 12, the display device 30 and/or a server that is accessible to either the scanner 12 or the display device 30. The result of the processing against the AI model 70 is the prediction of a preset that is most suitable for the body part 66 that is being scanned. In the example of FIG. 2, processing the control data frame 53 with the AI model results in a prediction that the control data frame 53 corresponds to a scan of a heart. As a result of this prediction, the AI model 70 may output an instruction to the scanner 12 to set a preset P2 (e.g., a cardiac preset) that is optimized for scanning a heart 66. It can be seen that the parameters for P2 (e.g. as illustrated, the depth and density of the vertical scan lines) are different from the parameters for preset P1. As illustrated, they are also different from reference parameters RP for the control data frame 53.

While not illustrated, other example parameters that may be different in different presets are the ultrasound energy and/or the average power usage of the scanner 12. For example, it may be the case that the AI model 70 predicts the suitable preset for the control data frame 53 is an obstetrics/gynecology preset or an ocular preset, meaning that the control data frames 53 may be scanning fetal tissue or eye tissue. Since these presets are generally also associated with limiting the power output of the ultrasound energy used during scanning to enhance safety for more sensitive tissue types, changing to the preset by the AI model 70 may also involve lower the ultrasound energy used for acquisition. In this manner, the embodiments described herein may provide enhanced safety measures, in addition to providing enhancements to operator workflow that reduce the manual step of selecting a preset.

After having switched the scanner 12 to use the preset P2 predicted by the AI model 70, the scanner 12 may continuing acquiring image data frames 54, 55 in sequence using parameters for preset P2. These image data frames 54, 55 may then be scan converted to ultrasound image frames 64, 65 respectively for viewing. As illustrated, the image frames 64, 65 acquired using preset P2 may be better optimized for viewing of the imaged anatomy (e.g., when acquiring images using the cardiac preset, the heart is shown more fully in view with clearer lines) as compared to image frames 60, 61, 62 acquired using preset P1.

To predict the settings that would suitable for a new control data frame 53, the AI model 70 may previously be generated using machine learning methods. For example, this may involve training the AI model with one or more datasets containing different classes of control data frames that have been labeled as being associated with various presets P1, P2, P3, P4 (shown in FIG. 2 with various label icons). These various presets may generally correspond to different types of anatomical features 74, 78, 82, 86. For example, the preset P1 may generally be for scanning lungs 74, preset P2 may generally be for scanning cardiac features 78, preset P3 may generally be for scanning bladders 82, and preset P4 may generally be for scanning abdominal features such as kidneys 86 or livers 88. In FIG. 2, the anatomical features 74, 78, 82, 86, 88 that the various presets P1-P4 are respectively associated with are shown in dotted outline for illustrative purposes to provide a pictorial representation of the anatomical features; but such pictorial representations are not viewable ultrasound image frames.

The embodiments herein may generally involve using the manually-selected preset under which an ultrasound data frame or an ultrasound image frame is acquired to train an AI model to predict the preset that would be suitable for a new ultrasound data frame or ultrasound image frame. While using such data to train an AI model may be workable, it is recognized there may be a mismatch between the training data (which were already manually-selected to be acquired under an optimal preset) and the new data that the AI model is to provide a prediction on (which may be acquired under a set of different unknown parameters). This mismatch may reduce the reliability of the predictions made by the AI model.

To improve the reliability of the AI model, in some embodiments, consistent reference parameters RP may be used to acquire the training data that is labeled and inputted into the AI model, as well as the new data that AI model is to predict the preset for. For example, this is shown in FIG. 2 where the various classes of the control data frames 72, 76, 80, 84 in the one or more datasets may be acquired using consistent reference parameters RP (which are generally similar to the reference parameters RP used to acquire the new control data frame 53 that the AI model 70 is to predict a preset for).

Notably, the consistent reference parameters RP are used even though the different presets P1-P4 (as associated with the different anatomical features 74, 78, 82, 86, 88) typically have their own associated different optimal parameters. By configuring both the training control data frames 72, 76, 80, 84 and a new control data frame 53 to be acquired using consistent reference parameters RP, there is no mismatch between the acquisition parameters of the training data and the data for which the AI model is to provide a prediction on. This may enhance the operation of the machine learning algorithms so that the AI model 70 can generate more reliable predictions about the preset that is suitable for a given new control data frame. This may also allow certain steps of normalizing the training data (e.g., for scan depth, resolution, contrast, brightness, image enhancements, noise reduction and the like) to be minimized. In various embodiments, the consistent reference parameters RP may have one or more of: a fixed depth, a fixed number of acquisition lines, fixed focal zones, a fixed sampling rate, fixed gain, fixed beamformer parameters, or fixed application of filters.

As shown in FIG. 2, the training is performed on control data frames 72, 76, 80, 84 similar to how a control data frame 53 (as opposed to a viewable ultrasound image frame) is fed into the AI model 70 for prediction. By performing the machine learning on pre-scan converted data frames 72, 76, 80, 84, 53, the act of scan converting control data frames into viewable ultrasound image frames may be avoided. This may enhance computational efficiency by reducing the computational effort required to perform scan conversion. Also, since pre-scan converted control data frames generally have a smaller memory footprint than post-scan converted ultrasound image frames, this may allow for increased throughput of various machine learning processes.

Notwithstanding, it is not required that the machine learning techniques described herein be performed on pre-scan converted data. In some embodiments, the methods described herein may be performed on post-scan converted images (e.g., on image data after the control data frames 53, 72, 76, 80, 84 are scan converted). In various embodiments, data frames (whether control data frames 72, 76, 80, 84 or scan converted image data frames) used as training data for the AI model 70 may include greyscale data. In various embodiments, these data frames used for training may also include Doppler data.

In various embodiments, the training control data frames 72, 76, 80, 84 may be acquired using the same model of ultrasound scanner 12 on which the AI model 70 will be deployed. However, in some embodiments, the model of ultrasound scanner used to acquire the training control data frames 72, 76, 80, 84 may differ from the model of ultrasound scanner 12 on which the AI model 70 is deployed (e.g., different manufacturer or design). This may be possible because consistent reference parameters RP are used for both the training control data frames 72, 76, 80, 84 and the new control data frame 53.

In some embodiments, the different models of ultrasound scanners 12 may even have different transducer array footprints (e.g., linear, curvilinear, or microconvex, or phased array) and/or different frequency ranges. This may be accomplished by configuring the control data frame 53 to use reference parameters RP that only acquire data lines from a center portion of the transducer array that are common to all transducer array footprint types, and by selecting an imaging frequency and depth that is common or overlaps amongst the different scanner types. Since the machine learning may be performed on pre-scan converted control data frames so that do not reflect any curvature of the transducer array footprint, using consistent reference parameters RP may allow the control data frame 53 acquired by the various scanner types to share enough common characteristics, so as to allow their various classifications to be applicable to other scanner models.

By controlling the parameters in this manner, the generated AI model 70 may be sufficiently robust to predict presets for a new control data frame 53 acquired from a scanner model 12 that is different from that which is used to acquire the training control data frames 72, 76, 80, 84.

As illustrated in FIG. 2, the AI model 70 may be trained with classes of control data frames 72, 76, 80, 84 that correspond to presets P1-P4 for scanning a single type of anatomy (e.g., for lungs 74, cardiac 78, or bladders 82), or multiple types of anatomy (e.g., an abdomen preset which may suitable for scanning kidneys 86 and livers 88).

In various embodiments, the different classes of ultrasound control data frames used for the AI model may generally include ultrasound data acquired for one or more anatomical features; such anatomical features including a lung, a heart, a liver, a kidney, a bladder, an eye, a womb, a thyroid gland, a breast, a brain, an artery, a vein, a muscle, an embryo, a tendon, a bone, a fetus, a prostate, a uterus, an ovary, testes, a pancreas, or a gall bladder.

In various embodiments, the different presets for which there may be labeled training control data frames may generally include presets for at least two of abdomen, cardiac, bladder, lung, obstetrics/gynecology, transcranial, superficial, thyroid, vascular, musculoskeletal, breast, ocular, prostate, fertility, or nerve.

Referring still to FIG. 2, the control data frames 53 that are collected are interspersed amongst the image data frames 50, 51, 52, 54, 55, and they may continue to be acquired in an interspersed fashion as the ultrasound scan proceeds. For example, there may be one control data frame 53 acquired for every three image data frames 50, 51, 52. Other interspersion rates are possible, and an interspersion rate may change during use of the scanner 12 (e.g., in some embodiments, control data frames 53 may be interleaved with image data frames 50, 51, 52, 54, 54).

The acquisition of the control data frames 53 may be configured to have minimal impact on the refresh rate of the image frames 60, 61, 62, 64, 65. In part this is because the processing of the control data frame 53 with the AI model 70 is performed on pre-scan converted image data, before being scan converted and placed into the image buffer. As a result, the image buffer may only have (not necessarily at the same time) image frames 60, 61, 62, 64, 65 that are going to be displayed, at regular intervals, so that the image refresh rate is uniform and the image feed appears smooth, without the acquisition and processing of the control data frames 53 causing any significant pause or interruption. The average acquisition rate of the image data frames, however, should be about equal to the refresh rate of the image that is displayed so that there is always enough data in the image buffer that the image refresh rate is not interrupted.

In various embodiments, the consistent reference parameters RP may be optimized to sufficiently allow for the machine learning processes described herein, while reducing the impact of the control data frames 53 on the image quality of ultrasound image frames 60, 61, 62, 64, 65. For example, the various parameters of the reference parameters RP may be configured to consume less resources (e.g., fewer lines, focal zones, or the like) so as to reduce their acquisition time, and their potential negative impact on frame rate.

Additionally or alternatively, in some embodiments, the reference parameters RP can be configured to minimize acquisition time of the control data frame 53 (e.g., by reducing the number of acquisition lines in a control data frame 53 versus the number of acquisition lines in an image data frame 50, 51, 52, 54, 55)

In some embodiments, during operation of the scanner 12, the user may be presented with a set of presets and an auto-preset option. While each preset is suited for a particular part of the anatomy, the auto-preset option, if selected, will automatically predict and select the optimum preset using the AI model 70 as described herein.

In some embodiments, the capture and analysis of the control data frame 53 may occur fast enough for the settings of the scanner 12 to be changed in time for the acquisition of the immediately following image data frame 54.

In some cases, the preset on the scanner 12 may be changed based on the predicted preset for a single control data frame 53. However, in some embodiments, the preset on the scanner 12 may be changed only after multiple control data frames 53 result in the same predicted preset. In this latter scenario, different configurations are possible. For example, it may be required that some consecutive number of control data frames 53 predict the same preset prior to the scanner 12 changing its preset. In another embodiment, the scanner 12 may change its preset after some percentage (e.g., 60-99%) of a past number of control data frames 53 provide the same predicted preset form the AI model 70.

Figure 3:
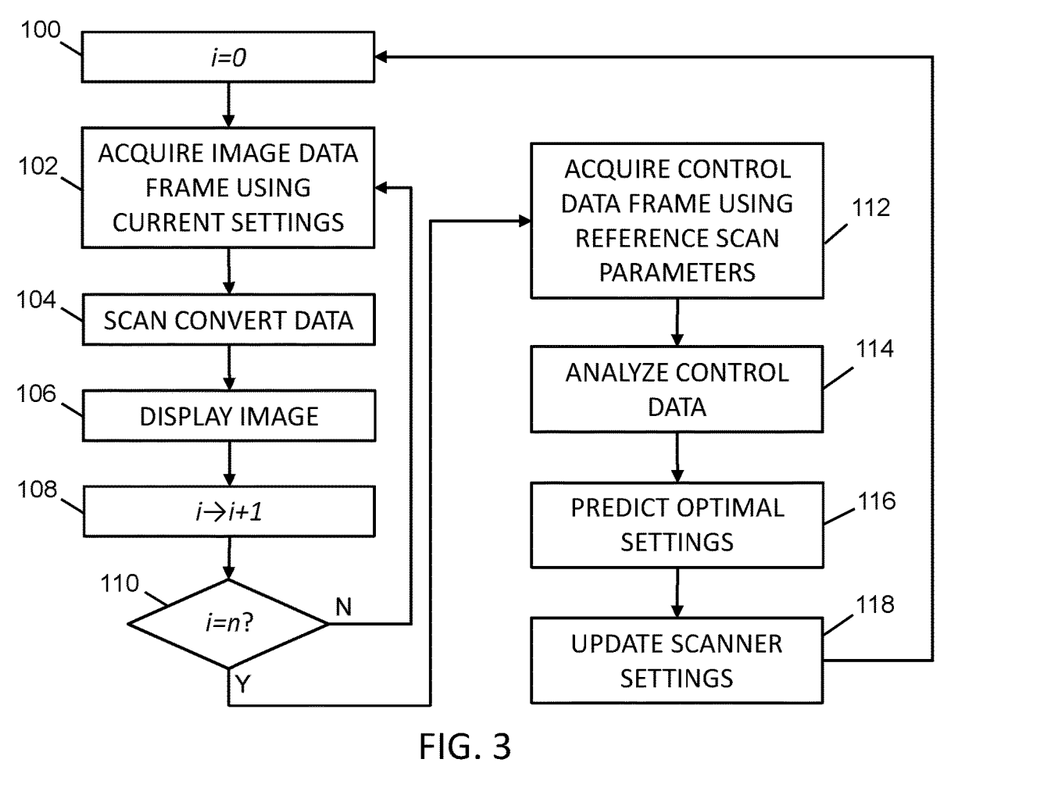
FIG. 3 is a flowchart for controlling an ultrasound scanner according to an embodiment of the present invention.

Referring to FIG. 3, a flowchart shows an exemplary process undertaken by the system 10 (as shown in FIG. 1), in which the scanner settings are updated as a result of analysis of a control data frame 53. In discussing FIG. 3, reference will also be generally made to the sequence of various frames shown in FIG. 2. In step 100, an image data frame counter is set to zero (i=0). In step 102, an image data frame 50 is acquired using whatever the current settings of the scanner 12 are. For example, the settings may be default settings, a particular preset, or settings that have been made manually. In step 104, the data in the image data frame 50 may be scan converted into a form suitable for display, following which the image frame 60 may be displayed in step 106. After the display of the image frame 60, the image data frame counter may be incremented in step 108. In step 110, the current value i of the data frame counter may be compared to a limit value n. If the value of the data frame counter is not yet equal to the limit value n, then the process reverts to step 102 in which another image data frame 51 is acquired. Steps 102-110 may be repeated, with subsequent image data frames being acquired, scan converted and displayed until the image data frame counter equals the limit value (i=n) in step 110.

When a series of n image data frames have been acquired (i=n), the process moves onto step 112, in which a control data frame 53 is acquired. The control data frame 53 may be acquired using the reference scan parameters, or reference settings, which are typically not the same as whatever the current settings were for step 102. In step 114, the control data frame present in the control data frame 53 may be analyzed, for example by processing it against the AI model 70. As a result of this processing, the AI model 70 may predict, in step 116, the optimal settings for the scanner 12 for the particular body part that is currently being scanned. In step 118, the settings of the scanner 12 may be updated. Updating the settings of the scanner 12 may entail changing from one preset to another preset (e.g., changing the settings from one value or set of values to another value or set of values). In other cases, updating the settings of the scanner 12 may entail changing the existing settings of the scanner 12 to those of a preset. In still other cases, the updating of the scanner settings may be to confirm that the present settings are already optimal and do not yet need to be changed.

After the scanner settings have been updated in step 118, which may or may not involve an actual change of the settings, the process may repeat from step 100.

Figure 4:
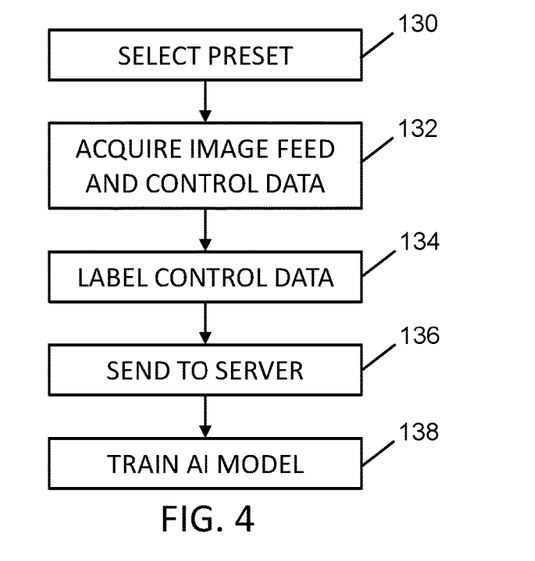
FIG. 4 is a flowchart for training an AI model, according to an embodiment of the present invention.

Referring to FIG. 4, a flowchart is shown for training the AI model 70. When discussing FIG. 4 below, reference will also be made to certain elements of FIGS. 1 and 2. In step 130, a preset of the scanner 12 is manually selected according to a type of body part that is to be scanned. In step 132, the scanner 12 acquires image data frames (e.g. 54, 55) and control data frames 53 that may be interspersed amongst the image data frames. The control data frames 53 are then labeled, in step 134, as being associated with the manually selected preset. The labeled control data frames may then be sent to a server, in step 136, where they are saved as training control data frames (e.g., control data frames 72, 76, 80, 84 as shown in FIG. 2). These training control data frames made be accessible to the AI model 70 for further training and/or re-enforcement. In step 138, the AI model 70 may be trained using the labeled control data frames that are stored in the server.

A common challenge in machine learning activities is obtaining labeled data that can be used to train an AI model 70. For example, if using a supervised learning technique, traditionally, human involvement may be needed to label which control data frames should be associated with which presets to generate suitable dataset that can be used to train the AI model. Such manual review and labeling is laborious, so as to make it difficult to create a large and robust dataset. However, by applying the method of FIG. 4 and inserting a control data frame 53 into the regular scanning activity performed by operators when using a scanner 12, the manual selection of the preset by the operators may be used as the human data labeling activity. For example, the method of FIG. 4 may be deployed on scanners 12 that do not have the AI model 70 enabled, so as to collect training data based on the presets selected by the operator. Then, once sufficient training data has been obtained and the AI model 70 trained, the AI model 70 may be deployed to enable the AI model-enabled preset prediction methods described herein.

Figure 5:
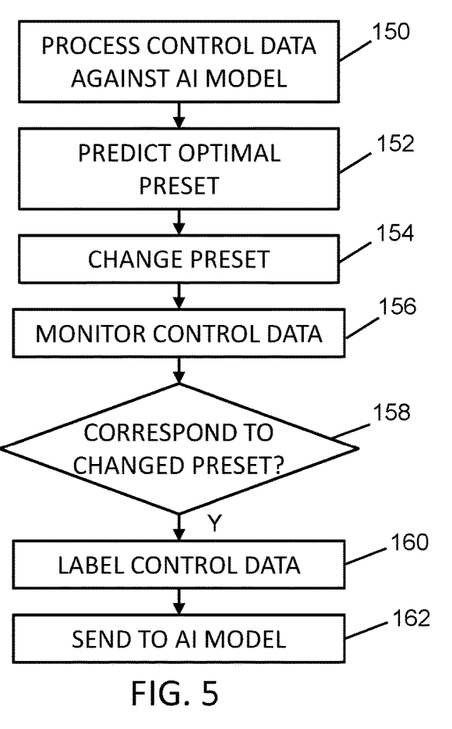
FIG. 5 is a flowchart for reinforcing an AI model, according to an embodiment of the present invention.

Referring to FIG. 5, a flowchart is shown for using and reinforcing the AI model 70. In discussing FIG. 5, reference will again also be made to the elements of FIG. 2. In some embodiments, during continued use of the ultrasound scanner 12 after a preset P2 has been predicted by the AI model 70 based on control data frame 53, subsequently acquired ultrasound control data frames may be used for further training or reinforcement of the AI model 70.

In step 150 of FIG. 5, the control data in a control data frame 53 may be processed against the AI model 70. In step 152, the AI model 70 predicts the optimal preset, and the preset of the scanner 12 may be changed in step 154. On a continuing basis, the control data acquired in subsequent interspersed control data frames is monitored may be step 156, by processing it against the AI model 70. For example, in the example of FIG. 2, acts 150-154 may be performed on a control data frame 53 against AI model 70. Referring back to FIG. 5, if, in step 158, after a period of time, the subsequent control data frames still correspond to the changed preset, then the subsequently obtained control data frames can be labeled, in step 160, as corresponding to the preset changed to in step 154. In step 162, the labeled control data frames may then be sent for storage in a location that is accessible by the AI model 70 for further training or reinforcement.

In some embodiments, in the auto-preset mode, the user interface on the display device 30 may be configured to show the new preset each time the preset is changed, and display an option for the user to cancel the change for a few seconds after the change. If used, the cancellation may be considered to be training data for the AI model 70. In the case of cancellation, the control data frames collected after the cancellation may be labeled as not corresponding to the preset predicted by the AI model 70 and sent to the server. If, within some period of time, a user manually selects a different preset after cancellation and the control data frames 53 continue to be similar to what was being acquired prior to cancellation, then the user-selected preset may also serve as training data for the AI model 70.

For example, it may be the case that the class of cardiac preset-related data in the original dataset used to train the AI model 70 lacks a four-chamber cardiac view, such that if control data frames for such an image is acquired for the first time during scanning, the AI model 70 fails to accurately predict use of the cardiac preset. If the user manually selects the cardiac preset while control data frames for such an image is being acquired (e.g., after cancelling selecting of a preset predicted by the AI model 70), then the control data frames for the four-chamber cardiac view may be added as training data so that the AI model 70 may learn that such control data frames are associated with a cardiac preset.

Figure 6:
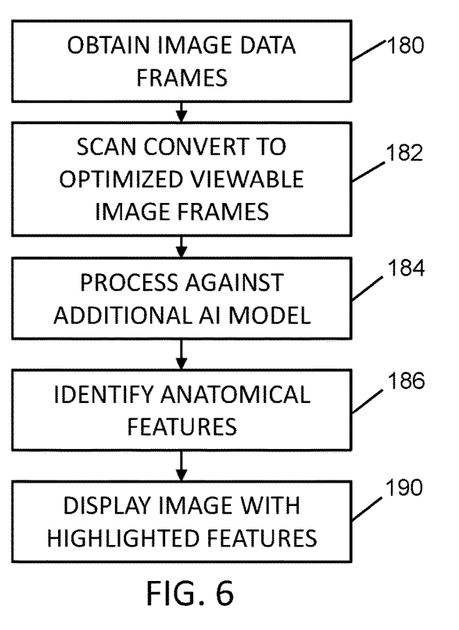
FIG. 6 is a flowchart for identifying features in an ultrasound image, according to an embodiment of the present invention.

Referring to FIG. 6, a flowchart is shown for identifying particular features in an ultrasound image 64, 65. In discussing FIG. 6, reference will also be made to the elements of FIGS. 1 and 2. Once the AI model 70 has predicted the optimal preset for the scanner 12, and the scanner 12 has been set to the predicted preset, then it may be possible to analyze the image frame 64, 65 that is used for viewing by an operator of the scanner 12. This further analysis may use an additional, separate AI model, which may be referred to as a micro-AI model, with the AI model 70 being referred to as a macro-AI model. The system 10 therefore may use two different AI models simultaneously, each applied to a different level of the ultrasound image acquisition process, the first being applied to control data frames 53 and the second being applied to image frames 64, 65 after the settings have been optimized using the first AI model.

In step 180 (which may, for example, be equivalent to multiple instances of step 102 in the method of FIG. 2 after cycling through steps 118 or 100), the system 10 may continue to acquire image data frames 54, 55 after the preset of the scanner 12 has been updated. As each image data frame is acquired, the scanner 12 may scan convert the image data frames to viewable image frames 64. 65, in step 182. The viewable image frames 64, 65 may then be processed against a second AI model (step 184) that is trained to identify (e.g., segment) anatomical features in the image frames 64, 65. In step 186, the second AI model may identify one or more anatomical features in the image frames 64, 65. The image frames 64, 65 may then be displayed with additional highlights, in step 190, to show where the identified anatomical features are in the images. Optionally, the highlighted areas may be annotated with the name of the anatomical feature or features that have been identified.

Figure 7:
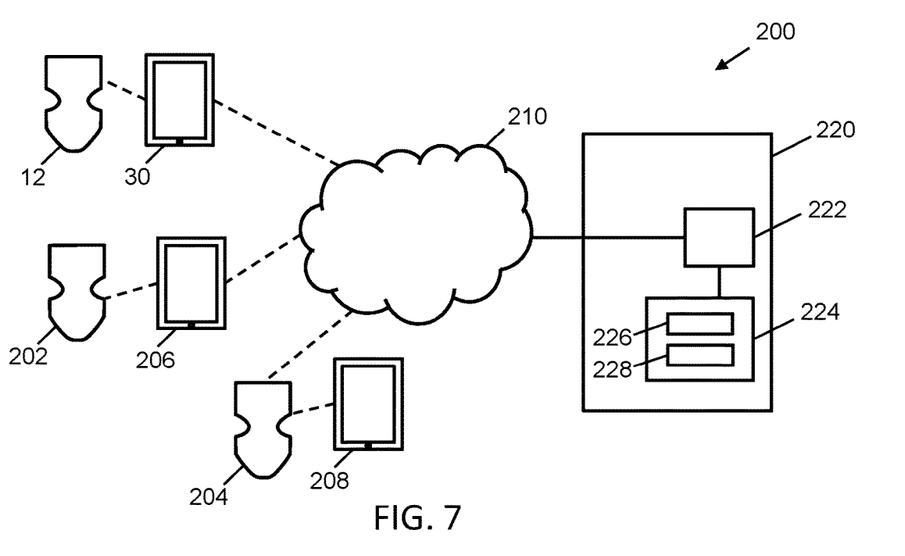
FIG. 7 is a schematic diagram of a further system according to an embodiment of the present invention.

Referring to FIG. 7, a system 200 is shown in which there are multiple similar or different scanners 12, 202, 204 connected to their corresponding display devices 30, 206, 208 and either connected directly, or indirectly via the display devices, to a network 210, such as the internet. The scanners 12, 202, 204 may be connected onwards via the network 210 to a server 220.

The server 220 may include a processor 222, which may be connected to a non-transitory computer readable memory 224 storing computer readable instructions 226, which, when executed by the processor 222, cause the server 220 to provide one or more of the functions of the system 200. Such functions may be, for example, the receiving of ultrasound data that may or may not be pre-processed, the scan conversion of ultrasound data that is received into an ultrasound image, the processing of ultrasound data in control data frames or image data frames, the control of the scanners 12, 202, 204, and/or machine learning activities related to one or more AI models. Such machine learning activities may include the training and/or reinforcing of one or more AI models.

Also stored in the computer readable memory 224 may be computer readable data 228, which may be used by the processor 222 in conjunction with the computer readable instructions 226 to provide the functions of the system 200. Computer readable data 228 may include, for example, settings for the scanners 12, 202, 204 such as preset parameters for acquiring ultrasound data depending on the analysis of control data frames, settings for user interfaces displayed on the display devices 30, 206, 208, and one or more AI models. For example, one AI model may be the AI model 70 that is used to analyze the control data frames 53, while another AI model may be used to analyze image frames 64, 65 for identifying anatomical features in the image frames 64, 65. Settings may also include any other data that is specific to the way that the scanners 12, 202, 204 operate or that the display devices 30, 206, 208 operate.

It can therefore be understood that the computer readable instructions and data used for controlling the system 200 may be located either in the computer readable memory of the scanners 12, 202, 204, the computer readable memory of the display devices 30, 206, 208, the computer readable memory 224 of the server 220, or any combination of the foregoing locations.

As noted above, even though the scanners 12, 202, 204 may be different, the control data frames that are captured by them are all captured with consistent reference parameters RP, so that each control data frame acquired may be used by the AI model 70 for training, without any special pre-processing of the captured data. Likewise, the control data frames acquired by the individual scanners 12, 202, 204 may all be processed against the AI model 70 directly for prediction of the optimal presets and/or for reinforcement of the AI model 70.

In some embodiments, AI models 70 present in the scanner 12 may be updated from time to time from an AI model present in the server 220.

In some embodiments, the analysis of the control data frames may be performed using a rules-based engine rather than an AI model.

Embodiments of the invention may be implemented using specifically designed hardware, configurable hardware, programmable data processors configured by the provision of software (which may optionally include 'firmware') capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs") and the like. Examples of configurable hardware are: one or more programmable logic devices such as programmable array logic ("PALs"), programmable logic arrays ("PLAs") and field programmable gate arrays ("FPGAs"). Examples of programmable data processors are: microprocessors, digital signal processors ("DSPs"), embedded processors, graphics processors, math co-processors, general purpose computers, server computers, cloud computers, main computers, computer workstations, and the like. For example, one or more data processors in a control circuit for a device may implement methods as described herein by executing software instructions in a program memory accessible to the processors.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The embodiments may also be provided in the form of a program product. The program product may include any non-transitory medium which carries a set of computer-readable instructions which, when executed by a data processor, cause the data processor to execute a method of the invention. Program products according to the invention may be in any of a wide variety of forms. The program product may include, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

Where a component (e.g. software, processor, support assembly, valve device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments. In some embodiments, the components of the systems and apparatuses may be integrated or separated. Moreover, the operations of the systems and apparatuses disclosed herein may be performed by more, fewer, or other components and the methods described may include more, fewer, or other steps. In other instances, well known elements have not been shown or described in detail and repetitions of steps and features have been omitted to avoid unnecessarily obscuring the invention. Screen shots may show more or less than the examples given herein. Accordingly, the specification is to be regarded in an illustrative, rather than a restrictive, sense.

It is therefore intended that the appended claims and claims hereafter introduced are interpreted to include all such modifications, permutations, additions, omissions and sub-combinations as may reasonably be inferred. The scope of the claims should not be limited by the embodiments set forth in the examples but should be given the broadest interpretation consistent with the description as a whole.

C. Interpretation of Terms

Unless the context clearly requires otherwise, throughout the description and the claims, the following applies:

In general, unless otherwise indicated, singular elements may be in the plural and vice versa with no loss of generality. The use of the masculine can refer to masculine, feminine or both.

The terms "comprise", "comprising" and the like are to be construed in an inclusive sense, as opposed to an exclusive or exhaustive sense, that is to say, in the sense of "including, but not limited to".

The terms "connected", "coupled", or any variant thereof, means any connection or coupling, either direct or indirect, between two or more elements; the coupling or connection between the elements can be physical, logical, or a combination thereof.

The words "herein," "above," "below" and words of similar import, when used in this application, refer to this application as a whole and not to any particular portions of this application.

The word "or" in reference to a list of two or more items covers all of the following interpretations of the word: any of the items in the list, all of the items in the list and any combination of the items in the list.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

To aid the Patent Office and any readers of any patent issued on this application in interpreting the claims appended hereto, applicant wishes to note that they do not intend any of the appended claims or claim elements to invoke 35 U.S.C. 112(f) unless the words "means for" or "step for" are explicitly used in the particular claim.

D. Claim Support

Disclosed herein is a method for controlling settings of an ultrasound scanner, the method comprising: acquiring an ultrasound image feed by sequentially obtaining ultrasound data frames that are converted to viewable image frames; and during acquisition of the ultrasound image feed: acquiring, using reference scan parameters, ultrasound control data frames that are interspersed amongst the ultrasound data frames, the reference scan parameters being consistently used for the interspersed ultrasound control data frames regardless of scan parameters that are used for acquiring the ultrasound image feed; and using the ultrasound control data frames to control the settings of the ultrasound scanner.

In some embodiments, the ultrasound control data frames are not converted to viewable image frames.

In some embodiments, the reference scan parameters consistently used for the interspersed ultrasound control data frames have one of: a fixed depth, a fixed number of acquisition lines, fixed focal zones or a fixed sampling rate.

In some embodiments, the acquiring the ultrasound image feed is performed according to a first preset, and the control of the settings of the ultrasound scanner comprises changing the first preset to a second preset different from the first preset.

In some embodiments, the ultrasound scanner outputs first ultrasound energy when operating according to the first preset, and the ultrasound scanner outputs second ultrasound energy when operating according to the second preset, and the second ultrasound energy has a lower power level than the first ultrasound energy.

In some embodiments, prior to changing the first preset to the second preset, at least the latest of the ultrasound control data frames is processed against an artificial intelligence model to predict a suitable preset for the ultrasound image feed, and the predicted suitable preset is used as the second preset that the ultrasound scanner is changed to.

In some embodiments, the artificial intelligence model is trained with one or more datasets containing different classes of ultrasound control data frames for different presets, and substantially all the ultrasound control data frames in the one or more datasets are consistently acquired using the reference scan parameters.

In some embodiments, the different presets comprise presets for at least two of abdomen, cardiac, bladder, lung, obstetrics/gynecology, transcranial, superficial, thyroid, vascular, musculoskeletal, breast, ocular, prostate, fertility, or nerve.

In some embodiments, the different classes of ultrasound control data frames comprise ultrasound data acquired of different body parts, the different body parts comprising at least two of: a lung, a heart, a liver, a kidney, a bladder, an eye, a womb, a thyroid gland, a breast, a brain, an artery, a vein, a muscle, an embryo, a tendon, a bone, a fetus, a prostate, a uterus, an ovary, testes, a pancreas, or a gall bladder.

In some embodiments, after changing from the first preset to the second preset, the method further comprises: acquiring additional ultrasound data frames according the second preset, the additional ultrasound data frames being converted to optimized viewable image frames; processing the optimized viewable image frames against an additional artificial intelligence model that identifies anatomical features in the optimized viewable image frames; and displaying the optimized viewable image frames with the anatomical features, as identified by the additional artificial intelligence model, highlighted.

In some embodiments, the method further comprises: monitoring subsequently acquired ultrasound control data frames to determine if the subsequently acquired ultrasound control data frames continue to correspond to the second preset; and after a period of time, labeling the subsequently acquired ultrasound control data frames as ultrasound control data frames that correspond to the second preset, so that the subsequently acquired ultrasound control data frames can used for training or reinforcing an artificial intelligence model.

Also disclosed herein is a method of labeling ultrasound images for input into an artificial intelligence model, comprising: operating an ultrasound scanner according to a user-selected preset; acquiring an ultrasound image feed by obtaining ultrasound data frames based on the user-selected preset; during acquisition of the ultrasound image feed, acquiring, using reference scan parameters, ultrasound control data frames that are interspersed amongst the ultrasound data frames, the reference scan parameters being consistently used for the interspersed ultrasound control data frames regardless of scan parameters that are defined for the user-selected preset; labeling the ultrasound control data frames as corresponding to the user-selected preset; and sending the labeled ultrasound control data frames to a server for adding to a dataset, wherein the dataset can be used to train the artificial intelligence model for predicting whether the user-selected preset would be suitable for later-acquired ultrasound control data frames.

Also disclosed herein is an ultrasound scanner that controls its settings, the ultrasound scanner comprising a processor and computer readable memory storing computer readable instructions, which, when executed by the processor, cause the ultrasound scanner to: acquire an ultrasound image feed by sequentially obtaining ultrasound data frames that are converted to viewable image frames; and during acquisition of the ultrasound image feed: acquire, using reference scan parameters, ultrasound control data frames that are interspersed amongst the ultrasound data frames, the reference scan parameters being consistently used for the interspersed ultrasound control data frames regardless of scan parameters that are used for acquiring the ultrasound image feed; and use the ultrasound control data frames to control the settings of the ultrasound scanner.

In some embodiments of the ultrasound scanner, the ultrasound control data frames are not converted to viewable image frames.

In some embodiments of the ultrasound scanner, the reference scan parameters consistently used for the interspersed ultrasound control data frames have one of: a fixed depth, a fixed number of acquisition lines, fixed focal zones or a fixed sampling rate.

In some embodiments the ultrasound scanner comprises: a first preset according to which the ultrasound image feed is acquired; and a second preset different from the first preset; wherein control of the settings of the ultrasound scanner comprises changing the first preset to the second preset.

In some embodiments of the ultrasound scanner, the ultrasound scanner outputs first ultrasound energy when operating according to the first preset, and the ultrasound scanner outputs second ultrasound energy when operating according to the second preset, and the second ultrasound energy has a lower power level than the first ultrasound energy.

In some embodiments the ultrasound scanner comprises an artificial intelligence model, wherein the ultrasound scanner is configured to: prior to changing the first preset to the second preset, process at least the latest of the ultrasound control data frames against the artificial intelligence model to predict a suitable preset for the ultrasound image feed; and use the predicted suitable preset as the second preset that the ultrasound scanner is changed to.

In some embodiments of the ultrasound scanner, the artificial intelligence model is trained with one or more datasets containing different classes of ultrasound control data frames for different presets, and substantially all the ultrasound control data frames in the one or more datasets are consistently acquired using the reference scan parameters.

In some embodiments of the ultrasound scanner, the different presets comprise presets for at least two of abdomen, cardiac, bladder, lung, obstetrics/gynecology, transcranial, superficial, thyroid, vascular, muscular, breast, ocular, prostate, fertility, or nerve.

In some embodiments of the ultrasound scanner, the different classes of ultrasound control data frames comprise ultrasound data acquired of different body parts, the different body parts comprising at least two of: a lung, a heart, a liver, a kidney, a bladder, an eye, a womb, a thyroid gland, a breast, a brain, an artery, a vein, a muscle, an embryo, a tendon, a bone, a fetus, a prostate, a uterus, an ovary, testes, a pancreas, or a gall bladder.

In some embodiments, the ultrasound scanner is further configured, after changing from the first preset to the second preset, to: acquire additional ultrasound data frames according the second preset, the additional ultrasound data frames being converted to optimized viewable image frames; process the optimized viewable image frames against an additional artificial intelligence model that identifies anatomical features in the optimized viewable image frames; and cause the optimized viewable image frames to be displayed with the anatomical features, as identified by the additional artificial intelligence model, highlighted.

In some embodiments, the ultrasound scanner is further configured to: monitor subsequently acquired ultrasound control data frames to determine if the subsequently acquired ultrasound control data frames continue to correspond to the second preset; and after a period of time, label the subsequently acquired ultrasound control data frames as ultrasound control data frames that correspond to the second preset, so that the subsequently acquired ultrasound control data frames can used for training or reinforcing an artificial intelligence model.

Also disclosed herein is an ultrasound scanner for labeling ultrasound images for input into an artificial intelligence model, comprising a processor and computer readable memory storing computer readable instructions, which, when executed by the processor, cause the ultrasound scanner to: operate according to a user-selected preset; acquire an ultrasound image feed by obtaining ultrasound data frames based on the user-selected preset; during acquisition of the ultrasound image feed, acquire, using reference scan parameters, ultrasound control data frames that are interspersed amongst the ultrasound data frames, the reference scan parameters being consistently used for the interspersed ultrasound control data frames regardless of scan parameters that are defined for the user-selected preset; label the ultrasound control data frames as corresponding to the user-selected preset; and send the labeled ultrasound control data frames to a server for adding to a dataset, wherein the dataset can be used to train the artificial intelligence model for predicting whether the user-selected preset would be suitable for later-acquired ultrasound control data frames.

Also disclosed is a system for controlling the settings of an ultrasound scanner; the system comprising: a server comprising an artificial intelligence model; an ultrasound scanner operably connected to the server, the ultrasound scanner comprising a processor and computer readable memory storing computer readable instructions, which, when executed by the processor, cause the ultrasound scanner to: acquire an ultrasound image feed by sequentially obtaining ultrasound data frames that are converted to viewable image frames; and during acquisition of the ultrasound image feed: acquire, using reference scan parameters, ultrasound control data frames that are interspersed amongst the ultrasound data frames, the reference scan parameters being consistently used for the interspersed ultrasound control data frames regardless of scan parameters that are used for acquiring the ultrasound image feed; and process at least the latest of the ultrasound control data frames against the artificial intelligence model to predict a suitable preset for the ultrasound image feed; and use the predicted suitable preset to control the settings of the ultrasound scanner by changing the ultrasound scanner from a first preset to a second preset.

In some embodiments of the system, the artificial intelligence model is trained with one or more datasets containing different classes of ultrasound control data frames for different presets, and substantially all the ultrasound control data frames in the one or more datasets are consistently acquired using the reference scan parameters.

In some embodiments of the system, the different presets comprise presets for at least two of abdomen, cardiac, bladder, lung, obstetrics/gynecology, transcranial, superficial, thyroid, vascular, muscular, breast, ocular, prostate, fertility, or nerve.

In some embodiments of the system, the different classes of ultrasound control data frames comprise ultrasound data acquired of different body parts, the different body parts comprising at least two of: a lung, a heart, a liver, a kidney, a bladder, an eye, a womb, a thyroid gland, a breast, a brain, an artery, a vein, a muscle, an embryo, a tendon, a bone, a fetus, a prostate, a uterus, an ovary, testes, a pancreas, or a gall bladder.

In some embodiments, the system comprised a display device operably connected to the ultrasound scanner, wherein: the ultrasound scanner is further configured, after changing from the first preset to the second preset, to acquire additional ultrasound data frames according the second preset, the additional ultrasound data frames being converted to optimized viewable image frames; the server is configured to process the optimized viewable image frames against an additional artificial intelligence model that identifies anatomical features in the optimized viewable image frames; and the display device displays the optimized viewable image frames with the anatomical features, as identified by the additional artificial intelligence model, highlighted.

In some embodiments, the system is further configured to: monitor subsequently acquired ultrasound control data frames to determine if the subsequently acquired ultrasound control data frames continue to correspond to the second preset; and after a period of time, label the subsequently acquired ultrasound control data frames as ultrasound control data frames that correspond to the second preset, so that the subsequently acquired ultrasound control data frames can used for training or reinforcing the artificial intelligence model.

The invention claimed is:

1. A method for controlling settings of an ultrasound scanner, the method comprising:
acquiring an ultrasound image feed by sequentially obtaining ultrasound data frames that are converted to viewable image frames; and
during acquisition of the ultrasound image feed:
acquiring, using reference scan parameters, ultrasound control data frames that are interspersed amongst the ultrasound data frames, the reference scan parameters being consistently used for the interspersed ultrasound control data frames regardless of scan parameters that are used for acquiring the ultrasound image feed, and wherein the ultrasound control data frames are not converted to viewable image frames; and
using the ultrasound control data frames to control the settings of the ultrasound scanner.

2. The method of claim 1, wherein the reference scan parameters consistently used for the interspersed ultrasound control data frames have one of: a fixed depth, a fixed number of acquisition lines, fixed focal zones or a fixed sampling rate.

3. The method of claim 1, wherein the acquiring the ultrasound image feed is performed according to a first preset, and the control of the settings of the ultrasound scanner comprises changing the first preset to a second preset different from the first preset.

4. The method of claim 3, wherein the ultrasound scanner outputs first ultrasound energy when operating according to the first preset, and the ultrasound scanner outputs second ultrasound energy when operating according to the second preset, and the second ultrasound energy has a lower power level than the first ultrasound energy.

5. The method of claim 3, wherein prior to changing the first preset to the second preset, at least the latest of the ultrasound control data frames is processed against an artificial intelligence model to predict a suitable preset for the ultrasound image feed, and the predicted suitable preset is used as the second preset that the ultrasound scanner is changed to.

6. The method of claim 5, wherein the artificial intelligence model is trained with one or more datasets containing different classes of ultrasound control data frames for different presets, and substantially all the ultrasound control data frames in the one or more datasets are consistently acquired using the reference scan parameters.

7. The method of claim 6, wherein the different presets comprise presets for at least two of abdomen, cardiac, bladder, lung, obstetrics/gynecology, transcranial, superficial, thyroid, vascular, musculoskeletal, breast, ocular, prostate, fertility, or nerve.

8. The method of claim 6, wherein the different classes of ultrasound control data frames comprise ultrasound data acquired of different body parts, the different body parts comprising at least two of: a lung, a heart, a liver, a kidney, a bladder, an eye, a womb, a thyroid gland, a breast, a brain, an artery, a vein, a muscle, an embryo, a tendon, a bone, a fetus, a prostate, a uterus, an ovary, testes, a pancreas, or a gall bladder.

9. The method of claim 5, wherein after changing from the first preset to the second preset, the method further comprises:
acquiring additional ultrasound data frames according the second preset, the additional ultrasound data frames being converted to optimized viewable image frames;
processing the optimized viewable image frames against an additional artificial intelligence model different from the artificial intelligence model for predicting a suitable preset, the additional artificial intelligence model for identifying anatomical features in the optimized viewable image frames; and
displaying the optimized viewable image frames with the anatomical features, as identified by the additional artificial intelligence model, highlighted.

10. The method of claim 3, further comprising:
monitoring subsequently acquired ultrasound control data frames to determine if the subsequently acquired ultrasound control data frames continue to correspond to the second preset; and
after a period of time, labeling the subsequently acquired ultrasound control data frames as ultrasound control data frames that correspond to the second preset, so that the subsequently acquired ultrasound control data frames can be used for training or reinforcing an artificial intelligence model.

11. A method of labeling ultrasound images for input into an artificial intelligence model, comprising:
operating an ultrasound scanner according to a user-selected preset;
acquiring an ultrasound image feed by obtaining ultrasound data frames based on the user-selected preset;
during acquisition of the ultrasound image feed, acquiring, using reference scan parameters, ultrasound control data frames that are interspersed amongst the ultrasound data frames, the reference scan parameters being consistently used for the interspersed ultrasound control data frames regardless of scan parameters that are defined for the user-selected preset, wherein the ultrasound control data frames are not converted to viewable image frames;
labeling the ultrasound control data frames as corresponding to the user-selected preset; and
sending the labeled ultrasound control data frames to a server for adding to a dataset, wherein the dataset can be used to train the artificial intelligence model for predicting whether the user-selected preset would be suitable for later-acquired ultrasound control data frames.

12. An ultrasound scanner that controls its settings, the ultrasound scanner comprising a processor and computer readable memory storing computer readable instructions, which, when executed by the processor, cause the ultrasound scanner to:
acquire an ultrasound image feed by sequentially obtaining ultrasound data frames that are converted to viewable image frames; and
during acquisition of the ultrasound image feed:
acquire, using reference scan parameters, ultrasound control data frames that are interspersed amongst the ultrasound data frames, the reference scan parameters being consistently used for the interspersed ultrasound control data frames regardless of scan parameters that are used for acquiring the ultrasound image feed, wherein the ultrasound control data frames are not converted to viewable image frames; and
use the ultrasound control data frames to control the settings of the ultrasound scanner.

13. The ultrasound scanner of claim 12, wherein the reference scan parameters consistently used for the interspersed ultrasound control data frames have one or more of: a fixed depth, a fixed number of acquisition lines, fixed focal zones or a fixed sampling rate.

14. The ultrasound scanner of claim 12, comprising:
a first preset according to which the ultrasound image feed is acquired; and
a second preset different from the first preset;
wherein control of the settings of the ultrasound scanner comprises changing the first preset to the second preset.

15. The ultrasound scanner of claim 14 comprising an artificial intelligence model, wherein the ultrasound scanner is configured to:
prior to changing the first preset to the second preset, process at least the latest of the ultrasound control data frames against the artificial intelligence model to predict a suitable preset for the ultrasound image feed; and
use the predicted suitable preset as the second preset that the ultrasound scanner is changed to.

16. The ultrasound scanner of claim 15, wherein the artificial intelligence model is trained with one or more datasets containing different classes of ultrasound control data frames for different presets, and substantially all the ultrasound control data frames in the one or more datasets are consistently acquired using the reference scan parameters.

17. The ultrasound scanner of claim 16, wherein the different presets comprise presets for at least two of abdomen, cardiac, bladder, lung, obstetrics/gynecology, transcranial, superficial, thyroid, vascular, musculoskeletal, breast, ocular, prostate, fertility, or nerve.

18. The ultrasound scanner of claim 16, wherein the different classes of ultrasound control data frames comprise ultrasound data acquired of different body parts, the different body parts comprising at least two of: a lung, a heart, a liver, a kidney, a bladder, an eye, a womb, a thyroid gland, a breast, a brain, an artery, a vein, a muscle, an embryo, a tendon, a bone, a fetus, a prostate, a uterus, an ovary, testes, a pancreas, or a gall bladder.

19. The ultrasound scanner of claim 14, further configured to:
monitor subsequently acquired ultrasound control data frames to determine if the subsequently acquired ultrasound control data frames continue to correspond to the second preset; and
after a period of time, label the subsequently acquired ultrasound control data frames as ultrasound control data frames that correspond to the second preset, so that the subsequently acquired ultrasound control data frames can be used for training or reinforcing an artificial intelligence model.

* * * * *